United States Patent
Centanni

(10) Patent No.: US 6,844,742 B2
(45) Date of Patent: Jan. 18, 2005

(54) METHOD AND APPARATUS FOR MEASURING CHEMICAL CONCENTRATION IN A FLUID

(75) Inventor: Michael A. Centanni, Parma, OH (US)

(73) Assignee: Steris Inc., Temecula, CA (US)

(*) Notice: Subject to any disclaimer, the term of this patent is extended or adjusted under 35 U.S.C. 154(b) by 0 days.

(21) Appl. No.: 10/389,036

(22) Filed: Mar. 14, 2003

(65) Prior Publication Data

US 2004/0178802 A1 Sep. 16, 2004

(51) Int. Cl.$^7$ .................. G01R 27/26; G01N 33/50

(52) U.S. Cl. ...................... 324/662; 204/403.01

(58) Field of Search .................... 204/403.01, 416, 204/431; 205/775, 777, 778.5, 782, 789; 422/82.01, 28; 324/666, 664, 663, 658, 665–668, 686–689, 610, 673, 680

(56) References Cited

U.S. PATENT DOCUMENTS

| | | | | |
|---|---|---|---|---|
| 3,636,444 A | * | 1/1972 | Strawn et al. ............... | 324/666 |
| 3,778,706 A | * | 12/1973 | Thompson .................. | 324/668 |
| 4,219,776 A | * | 8/1980 | Arulanandan ............... | 324/323 |
| 4,427,772 A | | 1/1984 | Kodera et al. ............... | 435/27 |
| 4,525,265 A | | 6/1985 | Abe et al. ................... | 204/403 |

(List continued on next page.)

OTHER PUBLICATIONS

U.S. Appl. No. 10/456,378, filed Jun. 6, 2003, Centanni, entitled: Method and Apparatus for Formulating and Controlling Chemical Concentrations in a Solution.
U.S. Appl. No. 10/456,380, filed Jun. 6, 2003, Centanni, entitled: Method and Apparatus for Formulating and Controlling Chemical Concentrations in a Gas Mixture.
U.S. Appl. No. 10/667,988, filed Sep. 22, 2003, Korenev et al., entitled: Method and Apparatus for Measuring The Concentration of Hydrogen Peroxide in a Fluid.
T. J. Buckley et al., "*Toroidal Cross Capacitor for Measuring the Dielectric Constant of Gases,*" Review of Scientific Instruments, vol. 71, No. 7, Jul. 2000, pp. 2914–2921.
Gross et al., "*The Dielectric Constants of Water Hydrogen Peroxide and Hydrogen Peroxide–Water Mixtures,*" L. Amer. Chem. Soc., vol. 72, 1950, pp. 2075–2080.
"*Humidity Sensor Theory and Behavior,*" Psychometrics and Moisture, Honeywell HVAC, Nov. 27, 2002.
Philipp, "*Charge Transfer Sensing,*" 1997.
Wojslaw, "*Everything You Wanted to Know About Digitally Programmable Potentiometers,*" Catalyst Semiconductor, Inc., Oct. 17, 2001, Publication No. 6009.
Kittel, "*Introduction to Solid State Physics,*" Fourth Edition, Jouhn Wiley & Sons, Inc., 1971.
Philipp, "*The Charge Transfer Sensor,*" Sensors Magazine, Oct. 1999.

*Primary Examiner*—Anjan Deb
*Assistant Examiner*—Amy He
(74) *Attorney, Agent, or Firm*—Kusner & Jaffe; Michael A. Centanni

(57) ABSTRACT

A chemical concentration detecting system for determining the relative concentrations of a multiple component chemical solution. The multi-component solution is preferably comprised of an antimicrobial chemical and a base fluid that acts as a diluent for the antimicrobial chemical, or as a vehicle or carrier for the antimicrobial chemical. A capacitor is exposed to the decontamination solution, wherein the decontamination solution acts as the dielectric between the plates of the capacitor. Permittivity of the dielectric is affected by the relative concentrations of the components, and thus a measurement of the capacitance is used to determine the relative concentration levels of the components in the solution.

52 Claims, 2 Drawing Sheets

U.S. PATENT DOCUMENTS

| | | |
|---|---|---|
| 4,674,879 A | 6/1987 | Gregorig et al. ............. 356/301 |
| 4,857,152 A | 8/1989 | Armstrong et al. .......... 204/1 T |
| 5,157,968 A | 10/1992 | Zfira ............................ 73/149 |
| 5,243,858 A | 9/1993 | Erskine et al. ............ 73/204.26 |
| 5,364,510 A | 11/1994 | Carpio .................... 204/153.1 |
| 5,439,569 A | 8/1995 | Carpio .................... 204/153.1 |
| 5,459,568 A | 10/1995 | Yano et al. .................. 356/336 |
| 5,470,754 A | 11/1995 | Rounbehler et al. ......... 436/106 |
| 5,600,142 A | 2/1997 | Van Den Berg et al. ...................... 250/339.13 |
| 5,847,276 A | 12/1998 | Mimken et al. ............... 73/453 |
| 5,882,590 A | 3/1999 | Stewart et al. ................. 422/28 |
| 6,369,387 B1 | 4/2002 | Eckles ........................ 250/343 |
| 6,454,874 B1 | 9/2002 | Jacobs et al. .................. 134/18 |
| 6,614,242 B2 | 9/2003 | Matter et al. ............... 324/698 |
| 2003/0063997 A1 | 4/2003 | Fryer et al. ..................... 422/3 |

* cited by examiner

METHOD AND APPARATUS FOR MEASURING CHEMICAL CONCENTRATION IN A FLUID

FIELD OF THE INVENTION

The present invention relates to determining chemical concentrations in a fluid, and more particularly to a method and apparatus for measuring the concentration of a chemical in a fluid comprised of multiple chemical components.

BACKGROUND OF THE INVENTION

The degree of polarity of a molecule is expressed in terms of a "dipole moment." Molecules, such as water, that exhibit a separation of charge within the molecule, have non-zero dipole moments. If the separated charges are equal in magnitude but opposite in sign, the magnitude of the dipole moment is equal to the product of the value of one of the separated charges and the distance of separation between the charges. The dipole moment is a vector that points from the negatively charged side of the molecule to the positively charged side of the molecule. The dipole moment depends on three factors, namely, (1) polarity of the molecule, (2) the magnitude of the separated charge, and (3) the geometry of the molecule. It is known that different molecules will have different dipole moments. For instance, molecules of antimicrobial chemicals, such as ozone ($O_3$), and hydrogen peroxide ($H_2O_2$), have different dipole moments than molecules of water ($H_2O$).

The present invention uses differences in the dipole moments of different molecules as a means for determining chemical concentrations in a multi-component fluid.

SUMMARY OF THE INVENTION

In accordance with the present invention, there is provided a chemical concentration detecting system for determining a concentration of a first component in a multi-component solution, comprising: (1) a capacitor having first and second plates exposed to the solution, said solution being a dielectric therebetween; and (2) processing means for determining a change in an electrical property of the capacitor, said change in the electrical property varying according to the concentration of the first component in the solution.

In accordance with another aspect of the present invention, there is provided a method for determining a concentration of a first component in a multi-component chemical solution, comprising the steps of: (1) exposing a capacitor, having first and second parallel plates, to the solution, said solution comprising a dielectric therebetween; and (2) determining a change in an electrical property of the capacitor, said change in the electrical property varying according to the concentration of the first component in the solution.

An advantage of the present invention is the provision of a concentration measuring system that uses a fluid as the dielectric of a capacitor.

Another advantage of the present invention is the provision of a concentration measuring system that will measure the concentration of a wide variety of chemicals, including antimicrobial chemicals.

Still another advantage of the present invention is the provision of a concentration measuring system that provides an accurate measurement of chemical concentrations in a fluid.

Yet another advantage of the present invention is the provision of a concentration measuring system that is simple and inexpensive to manufacture.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

While the present invention is described herein with reference to determination of a fluid concentration in a multi-component decontamination solution, it should be appreciated that the present invention finds utility in measuring a fluid concentration in other types of multi-component solutions, including solutions having multiple components wherein the dipole moments of the components differ.

Figure 1:
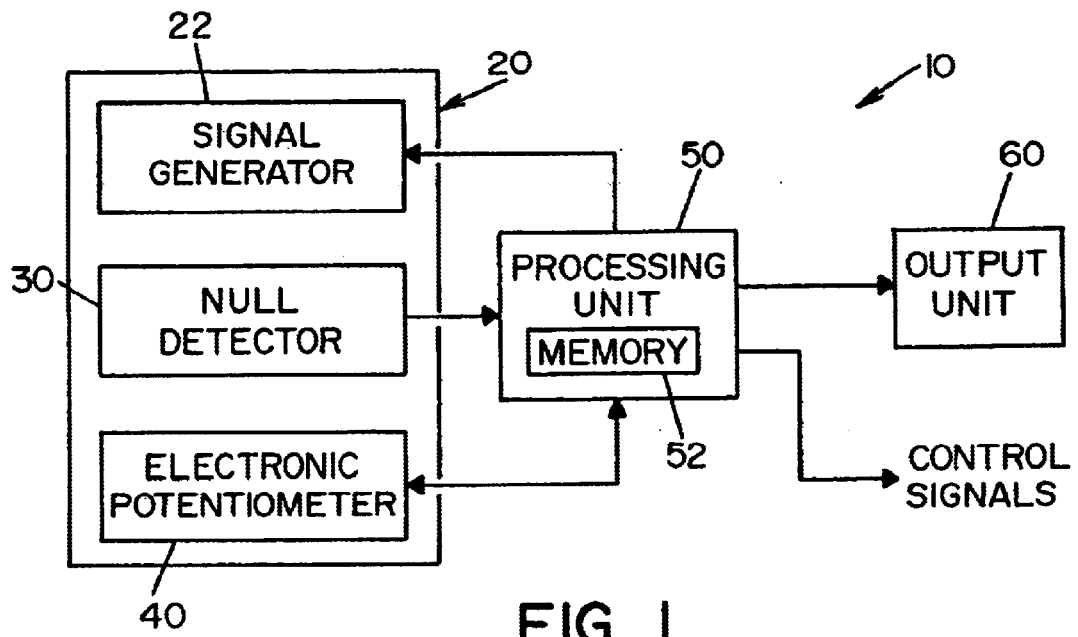
FIG. 1 is a block diagram of a chemical concentration detecting system, according to a preferred embodiment of the present invention.

Referring now to the drawings wherein the showings are for the purposes of illustrating a preferred embodiment of the invention only and not for purposes of limiting same, FIG. 1 shows a chemical concentration detecting system 10 according to a preferred embodiment of the present invention. Detecting system 10 is generally comprised of a sensor circuit 20, a processing unit 50 and an output unit 60.

Sensor circuit 20 uses a capacitor to sense concentration of chemicals in a multi-component fluid, as will be described in detail below. In this regard, it should be appreciated that the dielectric constant of a capacitor is dependent on electronic "polarizability." Polarization is the ability of molecules to form a dipole under an electric field or the ability of the electric field to line up or rotate an inherent dipole, such as water molecules.

In a preferred embodiment, processing unit 50 may take the form of a microcomputer or microcontroller, including a memory 52 for data storage. Processing unit 50 may also be used to control the operation of other system elements, such as flow controls for controlling fluid flow of components of a decontamination solution. Output unit 60 provides information in an audible and/or visual form. Accordingly, output unit 60 may take the form of an audio speaker and/or visual display unit.

Figure 2:
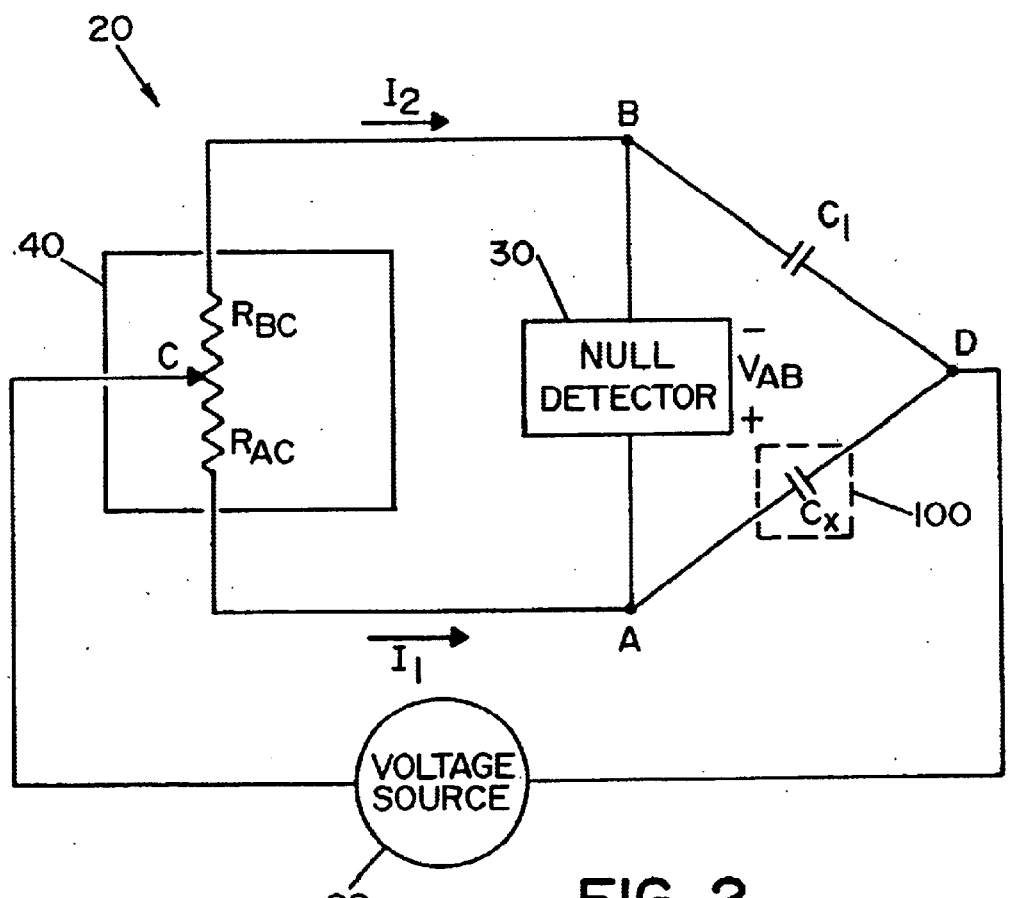
FIG. 2 is a schematic diagram illustrating a sensor circuit, according to a preferred embodiment of the present invention.

Referring now to FIG. 2, there is shown a detailed schematic of sensor circuit 20. In the preferred embodiment, sensor circuit 20 takes the form of a "bridge circuit." As is well known to those skilled in the art, bridge circuits are used to determine the value of an unknown impedance in terms of other impedances of known value. Highly accurate measurements are possible because a null condition is used to determine the unknown impedance. In the preferred embodiment, the bridge circuit is used to determine a capacitance value indicative of the concentration of chemicals in a multi-component fluid. In the embodiment shown in FIG. 2, sensor circuit 20 is generally comprised of a voltage source 22, a null detector 30, an electronic potentiometer 40, a capacitor $C_1$ of known capacitance, and a capacitor $C_x$. Capacitor $C_1$ is conventional capacitor located outside vessel, tank or chamber 100.

Capacitor $C_x$ is directly exposed to a decontamination solution having multiple chemical components. In this regard, capacitor $C_x$ is located ill a vessel, lank or chamber 100, wherein the decontamination solution fills the gap between the conducting plates of capacitor $C_x$, thereby acting as the insulator or "dielectric" of capacitor $C_x$. Sensor circuit 20 provides data indicative of a capacitance $C_x$, corresponding to a chemical concentration. In this regard, capacitance $C_x$ will vary in accordance with the concentration of components in the multi-component fluid.

In a preferred embodiment, capacitor $C_x$ is a parallel plate capacitor. However, it should be appreciated that capacitor $C_x$ could be constructed in a different form. For example, $C_x$ could be a cylindrical or spherical capacitor. If a spherical capacitor is used as capacitor $C_x$, holes must be placed in the outer shell of the capacitor such that the chemical components can enter and exit the capacitor.

Electronic potentiometer 40 functions in the same manner as a mechanical potentiometer. In this regard, electronic potentiometer 40 is a three terminal device. Between two of the terminals is a resistive element. The third terminal known as the "wiper" is connected to various points along the resistive element. The wiper is digitally controlled by processing unit 50 (see FIG. 1). The wiper divides the resistive element into two resistors $R_{BC}$ and $R_{AC}$. Electronic potentiometer 40 may take the form of a digitally programmable potentiometer (DPP™) available from Catalyst Semiconductor, Inc. of Sunnyvale, Calif.

In a preferred embodiment, voltage source 22 provides an AC voltage signal, such as a sinusoidal or pulse waveform. Null detector 30 is a device for detecting a null condition (i.e., a short circuit), such as a galvanometer, a voltmeter, a frequency-selective amplifier, and the like.

Operation of sensor circuit 20 will now be described in detail. The elements of the bridge circuit are connected between junctions AC, BC, AD, and BD. Electronic potentiometer 40 is operated by processing unit 50 to vary the resistances $R_{BC}$ and $R_{AC}$ until the potential difference between junctions A and B ($V_{AB}$) is zero. When this situation exists, the bridge is said to be balanced or is "nulled." The following relationships then hold for voltages in the main branches:

$$V_{AC}=V_{BC}, \text{ and } V_{AD}=V_{BD},$$

where $V_{AC}$ is the voltage between junctions A and C, $V_{BC}$ is the voltage between junctions B and C, $V_{AD}$ is the voltage between junctions A and D, and $V_{BD}$ is the voltage between junctions B and D. Accordingly, $$V_{AD}/V_{AC}=V_{BD}/V_{BC}$$

$$V_{AD}=V_{BD}/(V_{AC}/V_{BC})$$

The capacitance of capacitor $C_x$ is connected between junctions A and D with a known capacitance of capacitor $C_1$ between junctions B and D. Electronic potentiometer 40, connected from junction A to junction C to junction B, is adjusted by processing unit 50 to vary the voltages $V_{AC}$ and $V_{BC}$.

When a null is detected by null detector 30, current $I_1$ flows from junction C to junction A to junction D, and a current $I_2$ flows from junction C to junction B to junction D. The voltage $V_{AC}$ across junctions A to C, and the voltage $V_{BC}$ across junctions B to C are:

$$V_{AC}=I_1R_{AC} \text{ and } V_{BC}=I_2R_{BC}.$$

The voltage across a capacitor with capacitance C, current I, and frequency is:

$$V = \frac{I}{2\pi fC}$$

Therefore, the voltages $V_{AD}$ and $V_{BD}$ may be expressed as:

$$V_{AD} = \frac{I_1}{2\pi fC_x}$$

$$V_{BD} = \frac{I_2}{2\pi fC_1}$$

As discussed above, $V_{AD}=V_{BD}/(V_{AC}/V_{BC})$, $V_{AC}=I_1R_{AC}$, and $V_{BC}=I_2R_{BC}$. Therefore, $$C_x = C_1\left(\frac{R_{BC}}{R_{AC}}\right).$$

In view of the forgoing relationship, when a null condition is detected, the resistance values for $R_{BC}$ and $R_{AC}$, along with the known capacitance value of capacitor $C_1$, can be used to determine unknown value of capacitance for capacitor $C_x$.

Chemical concentration detecting system 10 utilizes differences in dipole moments of different molecules to determine the relative concentration of a chemical in a solution. As discussed above, the decontamination solution tills the gap between the conducting plates of capacitor $C_x$, thereby acting as the dielectric of capacitor $C_x$. By configuring capacitor $C_x$ as an element of a bridge circuit, a measure of resistance values $R_{AC}$ and $R_{BC}$, when the bridge is balanced or nulled, can be used to determine the capacitance of capacitor $C_x$. The capacitance of capacitor $C_x$ is indicative of the relative concentrations of the chemical components in the decontamination solution, since the permittivity of the respective dielectric is affected by the relative concentrations of the chemical components of the decontamination) solution.

It is well known that for a parallel plate capacitor $C=(k\epsilon_0)(A/d)=(\epsilon)(A/d)$, where C is capacitance, k is the dielectric constant, $\epsilon_0$ is the permittivity of free space ($8.85\times10^{-12}$ F/m), $\epsilon$ is the permittivity (Farads/meter) of the capacitor dielectric, A is the area of the capacitor plates (m$^2$), and d is the separation in meters between the capacitor plates. As $\epsilon$ increases, the capacitance C will increase. Where the capacitor is a parallel plate capacitor with circular plates of diameter D, $C=(\pi D^2\epsilon)/(4d)$.

It will be appreciated that the dielectric constant k of the capacitor can be determined according to the following expression:

$$k = \frac{4dC}{\pi D^2\epsilon_0},$$

where the value of capacitance, C, is determined as discussed above. The dielectric constant of the capacitor can also be determined by determining the capacitance with the dielectric in place between the conducting plates ($C_d$), and then determine the capacitance without the dielectric in place ($C_o$). The ratio of the two capacitances equals the dielectric constant, $$k = \frac{C_d}{C_0}.$$

The response of a capacitor is influenced by the characteristics (e.g., frequency) of the AC waveform applied thereto. In this regard, capacitive reactance ($X_c$) is a function of frequency. Capacitive reactance is the opposition offered to the flow of alternating current by pure capacitance, and is expressed in ohms ($X_c=1/(2\pi fC)$). Accordingly, frequency of the waveform generated by voltage source 22 influences the response of capacitors. Thus, the frequency selected for voltage source 22 should preferably be a frequency that will provide a generally linear response for capacitance as the concentration of a chemical component is varied. This will facilitate the use of interpolation and extrapolation of capacitance values, as will be discussed further below. If a suitable linear response is not obtained, then all expanded set of data points should be stored in memory 52.

Figure 3:
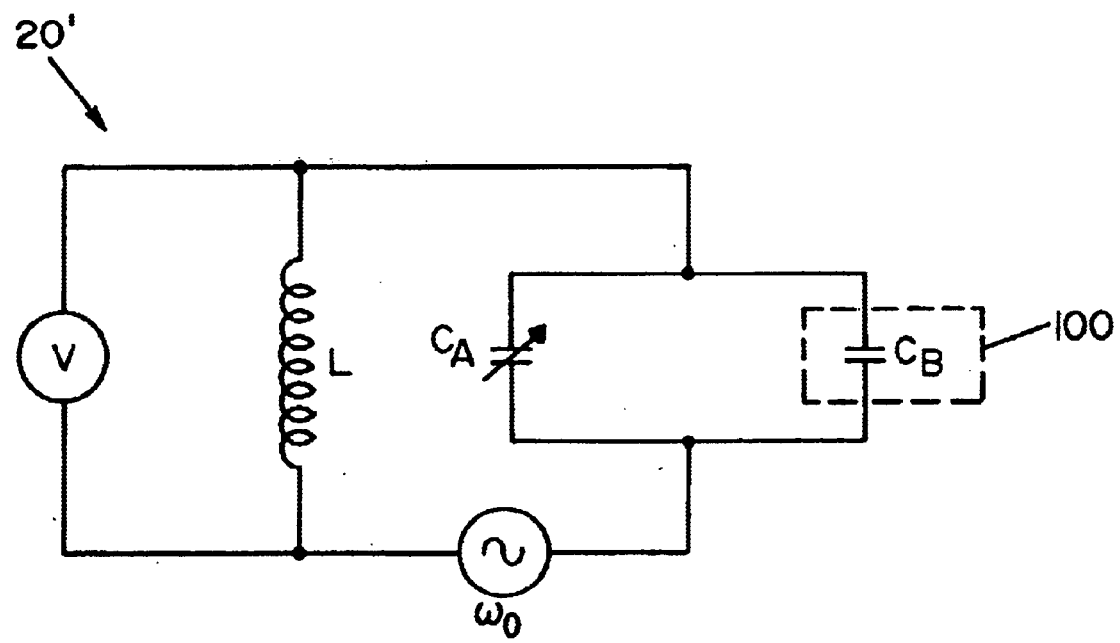
FIG. 3 is a schematic diagram illustrating a sensor circuit, according to an alternative embodiment of the present invention.

It should be appreciated that while a preferred embodiment of the present invention includes a sensor circuit 20 in the form of a bridge circuit, other types of circuits and techniques (including other types of bridge circuits, and capacitance meters) known to those skilled in the art, may be suitably used to measure capacitance. For example, FIG. 3 illustrates an alternative sensor circuit 20'. Sensor circuit 20' is an LC resonant circuit, having a variable capacitor $C_A$ located outside vessel 100, and a capacitor $C_B$ directly exposed to a decontamination solution having multiple chemical components. In this regard, capacitor $C_B$ is located in vessel 100, wherein the decontamination solution fills the gap between the conducting plates of capacitor $C_B$, thereby acting as the insulator or "dielectric" of capacitor $C_B$. Since the resonance frequency $\omega_0 = [L(C_A+C_B)]^{-1/2}$, the unknown capacitance of capacitor $C_B$ can be determined.

With reference to FIGS. 1 and 2, operation of chemical concentration detecting system 10, according to a preferred embodiment, will now be described in detail. As a preliminary step, processing unit 50 stores in memory 52 a set of data comprising values of the capacitance of capacitor $C_x$ for a plurality of relative concentrations of a multi-component decontamination solution. This set of data may be determined by exposing capacitor $C_x$ of system 10 to several different combinations of relative concentrations of the multi-component decontamination solution, and recording the corresponding measured capacitance $C_x$. For example, processing unit 50 may store values of the capacitance of capacitor $C_x$ that are determined for a plurality of relative concentrations of a multi-component decontamination solution comprised of only two components. As the relative concentrations of the first and second components are varied, the corresponding capacitance of capacitor $C_x$ is determined, and stored in memory 52. For instance, capacitance of capacitor $C_x$ may be determined for various concentrations of a first component and a second component (at a fixed volume of the decontamination solution) including, but not limited to:

0% first component and 100% second component,
25% first component and 75% second component,
50% first component and 50% second component,
75% first component and 25% second component, and
100% first component and 0% second component.

After the set of data is stored in memory 52, measurement of concentrations of a multi-component decontamination solution can commence. Capacitor $C_x$ is exposed to a multi-component decontamination solution that is being monitored. As indicated above, capacitor $C_x$ may be located in a vessel, tank or chamber 100 filled with the multi-component solution. A determination of $R_{AC}$ and $R_{BC}$ when the bridge is nulled is then used to determine a value for the capacitance of capacitor $C_x$. As discussed above, $C_x=C_1$ ($R_{BC}/R_{AC}$). The data stored in memory 52 is searched for the capacitance of capacitor $C_x$ to obtain the corresponding relative concentrations. A linear relationship between concentration and capacitance allows one to normalize any measurement made so as to provide the absolute concentration of each component in the solution. If the capacitance of capacitor $C_x$ is not found in the pre-stored data, the stored data may be interpolated or extrapolated to obtain a concentration corresponding to the measure capacitance of capacitor $C_x$. As noted above, frequency of the waveform generated by voltage source 22 will influence the response of capacitors. Where the capacitance of capacitor $C_x$ does not exhibit a suitable linear response, an expanded set of data points should be stored in memory 52, so that interpolation or extrapolation is unnecessary.

It should be appreciated that while a preferred embodiment of the present invention uses a measure of a capacitor's capacitance to determine relative concentrations, it is also contemplated that a measure of other electrical properties of a capacitor may be used to determine relative concentrations, including, but not limited to, the permittivity and dielectric constant of the capacitor dielectric.

Based upon the determined relative concentrations, processing unit 50 may be programmed to control the concentration of one or more components of the decontamination solution. For instance, processing unit 50 may output control signals (see FIG. 1) to adjust a flow control valve or other control means for modifying the relative concentrations. Accordingly, processing unit 50 may provide feedback control to adjust the relative concentrations to correspond with desired relative concentrations that provide optimum decontamination. Processing unit 50 may also output signals to output unit 60 to provide an audible and/or visual indicator when the determined relative concentrations are not within a desired range. The visual indicator may assist an operator by including a display of the relative concentrations or absolute concentration of an oxidant or sterilant as determined by processing unit 50.

In a preferred embodiment, the multi-component decontamination solution is comprised of two components, namely, an antimicrobial chemical and a base fluid. The antimicrobial chemical is the active chemical for a decontamination process, while the base fluid acts as a diluent for the antimicrobial chemical, or as a vehicle or carrier for the antimicrobial chemical.

Examples of antimicrobial chemicals, include, but are not limited to, liquids, such as hydrogen peroxide, peracids such as peracetic acid, and bleach, as well as gases, such as ozone, ammonia, ethylene oxide, fluorine containing chemicals, chlorine containing chemicals, and other highly oxidative gases.

Examples of base fluids, include, but are not limited to, water, deionized water, distilled water, an alcohol (e.g., a tertiary alcohol), a glycol-containing chemical compound, and a mixture thereof. Glycol-containing chemical compounds include, but are not limited to, polyethylene glycol, diethylene glycol, triethylene glycol, tetraethylene glycol, glycol ethers, polypropylene glycol, propylene glycol, and combinations thereof.

Some typical combinations of an antimicrobial chemical and a base fluid, include, but are not limited to, hydrogen peroxide and water, bleach and water, ozone and water, peracid and water, peracetic acid and water, alcohol and water, and ozone dissolved in a glycol, or an alcohol, such as a tertiary alcohol.

It is contemplated that the present invention may also be suitably used in a decontamination process to determine whether rinse water during a decontamination process "rinse cycle" is devoid of ail antimicrobial chemical. In this regard, measured capacitance can be used to assure that no measurable, residual, antimicrobial chemical is to be found in the rinse water. Furthermore, any other chemicals that are present in measurable concentrations would be indicated by the measured capacitance. Visual and/or audible signals may alert the operator that objects (e.g., medical instruments), undergoing a decontamination process may not be clean or sterile.

In an alternative embodiment of the present invention, two sensor circuits 20 are used. Capacitor $C_{x1}$ of the first sensor circuit 20 is exposed to a chemical solution comprised of first and second chemical components (e.g., a solution of an antimicrobial chemical and a base fluid). Capacitor $C_{x2}$ of the second sensor circuit 20 is exposed only to the second component of the two-component chemical solution (e.g., the base fluid). Processing unit 50 calculates the difference between the two measured capacitances $C_{x1}$ and $C_{x2}$ to determine the concentration of the first chemical component of the solution. In this regard, the difference in capacitances $C_{x1}$ and $C_{x2}$ will be attributable to the concentration of the first chemical component.

Other modifications and alterations will occur to others upon their reading and understanding of the specification. It is intended that all such modifications and alterations be included insofar as they come within the scope of the invention as claimed or the equivalents thereof.

What is claimed is:

1. A chemical concentration detecting system for determining a concentration of an antimicrobial chemical component in a multi-component decontamination solution comprised of the antimicrobial chemical component and a base fluid, said system comprising:
    a capacitor having first and second plates exposed to the decontamination solution, said decontamination solution comprising a dielectric therebetween; and
    processing means for determining a sensed electrical properly value of the capacitor, said sensed electrical property value varying according to the concentration of the antimicrobial chemical component in the decontamination solution,
    wherein said antimicrobial chemical component is selected from a group consisting of: hydrogen peroxide, peracid, peracetic acid, bleach, ozone, ammonia, ethylene oxide, a fluorine containing chemical, and a chlorine containing chemical.

2. A chemical concentration detecting system according to claim 1, wherein said capacitor is selected from the group consisting of: a parallel plate capacitor, a cylindrical capacitor, and a spherical capacitor.

3. A chemical concentration detecting system according to claim 1, wherein said processing means includes a memory for storing a set of data including electrical property values and corresponding concentration values indicative of the relative concentration of the antimicrobial chemical component in the decontamination solution.

4. A chemical concentration detecting system according to claim 3, wherein said processing means uses the sensed electrical property value to obtain a relative concentration from said set of data.

5. A chemical concentration detecting system according to claim 4, wherein said processing means normalizes said relative concentration to provide an absolute concentration of the antimicrobial chemical component of the decontamination solution.

6. A chemical concentration detecting system according to claim 3, wherein said processing means uses said set of data to interpolate or extrapolate a relative concentration corresponding to the sensed electrical property value.

7. A chemical concentration detecting system according to claim 1, wherein said antimicrobial chemical component is hydrogen peroxide.

8. A chemical concentration detecting system according to claim 7, wherein said antimicrobial chemical is selected from a group consisting of: a liquid and an oxidative gas.

9. A chemical concentration detecting system according to claim 1, wherein said base fluid is at least one of: (a) a diluent for the antimicrobial chemical component, and (b) a vehicle for the antimicrobial chemical component.

10. A chemical concentration detecting system according to claim 1, wherein said antimicrobial chemical component is peracid.

11. A chemical concentration detecting system according to claim 1, wherein said antimicrobial chemical component is peracetic acid.

12. A chemical concentration detecting system according to claim 1, wherein said system further comprises:
    a bridge circuit, wherein said capacitor forms a part of said bridge circuit.

13. A chemical concentration detecting system according to claim 12, wherein said bridge circuit includes a potentiometer having first and second resistances associated therewith, said processing means determining values of said first and second resistances when the bridge circuit is in a null condition to determining said sensed electrical property value.

14. A method for determining a concentration of an antimicrobial chemical component in a multi-component decontamination solution composed of the antimicrobial chemical component and a base fluid, the method comprising the steps of:
    exposing a capacitor, having first and second plates, to the decontamination solution, said decontamination solution comprising a dielectric therebetween;
    sensing an electrical property of the capacitor to obtain a sensed electrical property value, said sensed electrical property value varying according to the concentration of the antimicrobial chemical component in the decontamination solution; and
    determining the concentration of the antimicrobial chemical component in accordance with said sensed electrical property value,
    wherein said antimicrobial chemical component is selected from a group consisting of: hydrogen peroxide, peracid, peracetic acid, bleach, ozone, ammonia, ethylene oxide, a fluorine containing chemical, and a chlorine containing chemical.

15. A method according to claim 14, wherein said step of determining the concentration of the antimicrobial chemical component in accordance with said sensed electrical property value includes:
    accessing pre-stored data including electrical property values and corresponding concentration values indicative of the concentration of the antimicrobial chemical component in the decontamination solution.

16. A method according to claim 15, wherein said step of determining the concentration of the antimicrobial chemical component in accordance with said sensed electrical property value includes:
interpolating or extrapolating from the pre-stored data the concentration of the antimicrobial chemical component in the decontamination solution.

17. A method according to claim 15, wherein said step of determining the concentration of the antimicrobial chemical component in accordance with said sensed electrical property value includes:
normalizing said concentration of the antimicrobial chemical component to provide an absolute concentration of the antimicrobial chemical component of said decontamination solution.

18. A method according to claim 14, wherein said antimicrobial chemical component is hydrogen peroxide.

19. A method according to claim 14, wherein said base fluid is at least one of: (a) a diluent for the antimicrobial chemical component, and (b) a vehicle for the antimicrobial chemical component.

20. A method according to claim 14, wherein said antimicrobial chemical component is peracid.

21. A method according to claim 14, wherein said antimicrobial chemical component is peracetic acid.

22. A method according to claim 14, wherein said base fluid is selected from a group consisting of: water, an alcohol, a glycol-containing chemical compound, and combinations thereof.

23. A method according to claim 22, wherein said glycol-containing chemical compound is selected for a group consisting of: polyethylene glycol, diethylene glycol, triethylene glycol, tetraethylene glycol, glycol ethers, polypropylene glycol, propylene glycol, and combinations thereof.

24. A method according to claim 22, wherein said alcohol is a tertiary alcohol.

25. A method for determining a concentration of an antimicrobial chemical component in a multi-component decontamination solution comprised of the antimicrobial chemical component and a base fluid, the method comprising the steps of:
exposing a capacitor, having first and second plates, to the decontamination solution, said decontamination solution comprising a dielectric therebetween;
sensing an electrical property of the capacitor to obtain a sensed electrical property value, said sensed electrical property value varying according to the concentration of the antimicrobial chemical component in the decontamination solution;
accessing pre-stored data including electrical property values and corresponding concentration values indicative of the concentration of the antimicrobial chemical component in the decontamination solution; and
determining the concentration of the antimicrobial chemical component in accordance with said pre-stored data.

26. A method according to claim 25, wherein said step of determining the concentration of the antimicrobial chemical component in accordance with said pre-stored data includes:
interpolating or extrapolating from the pre-stored data the concentration of the antimicrobial chemical component in the decontamination solution.

27. A method according to claim 25, wherein said step of determining the concentration of the antimicrobial chemical component in accordance with said pre-stored data includes:
normalizing said concentration of the antimicrobial chemical component to provide an absolute concentration of the antimicrobial chemical component of said decontamination solution.

28. A method according to claim 25, wherein said antimicrobial chemical component is selected from a group consisting of: hydrogen peroxide, peracid, peracetic acid, bleach, ozone, ammonia, ethylene oxide, a fluorine containing chemical, and a chlorine containing chemical.

29. A method according to claim 25, wherein said base fluid is at least one of: (a) a diluent for the antimicrobial chemical component, and (b) a vehicle for the antimicrobial chemical component.

30. A method according to claim 25, wherein said base fluid is selected from a group consisting of: water, an alcohol, a glycol-containing chemical compound, and combinations thereof.

31. A method according to claim 30, wherein said glycol-containing chemical compound is selected from a group consisting of: polyethylene glycol, diethylene glycol, triethylene glycol, tetraethylene glycol, glycol ethers, polypropylene glycol, propylene glycol, and combinations thereof.

32. A method according to claim 30, wherein said alcohol is a tertiary alcohol.

33. A chemical concentration detecting system for determining a concentration of an antimicrobial chemical component in a multi-component decontamination solution comprised of the antimicrobial chemical component and a base fluid, said system comprising:
a capacitor having fist and second plates exposed to the decontamination solution, said decontamination solution comprising a dielectric therebetween;
processing means for determining a sensed electrical property value of the capacitor, said sensed electrical properly value varying according to the concentration of the antimicrobial chemical component in the decontamination solution; and
a memory for storing a set of data including electrical property values and corresponding concentration values indicative of the relative concentration of the antimicrobial chemical component in the decontamination solution.

34. A chemical concentration detecting system according to claim 33, wherein said antimicrobial chemical component is selected from a group consisting of: hydrogen peroxide, peracid, peracetic acid, bleach, ozone, ammonia, ethylene oxide, a fluorine containing chemical, and a chlorine containing chemical.

35. A chemical concentration detecting system according to claim 33, wherein said antimicrobial chemical component is hydrogen peroxide.

36. A chemical concentration detecting system according to claim 33, wherein said antimicrobial chemical component is peracid.

37. A chemical concentration detecting system according to claim 33, wherein said antimicrobial chemical component is peracetic acid.

38. A chemical concentration detecting system according to claim 33, wherein said base fluid is at least one of: (a) a diluent for the antimicrobial chemical component, and (b) a vehicle for the antimicrobial chemical component.

39. A method according to claim 33, wherein said base fluid is selected from a group consisting of: water, an alcohol, a glycol-containing chemical compound, and combinations thereof.

40. A chemical concentration detecting system according to claim 39, wherein said glycol-containing chemical compound is selected from a group consisting of: polyethylene glycol, diethylene glycol, triethylene glycol, tetraethylene glycol, glycol ethers, polypropylene glycol, propylene glycol, and combinations thereof.

41. A chemical concentration detecting system according to claim 39, wherein said alcohol is a tertiary alcohol.

42. A chemical concentration detecting system according to claim 33, wherein said antimicrobial chemical is selected from a group consisting of: a liquid and an oxidative gas.

43. A chemical concentration detecting system according to claim 33, wherein said capacitor is selected from the group consisting of: a parallel plate capacitor, a cylindrical capacitor, and a spherical capacitor.

44. A chemical concentration detecting system according to claim 33, wherein said processing means uses the sensed electrical property value to obtain a relative concentration from said set of data.

45. A chemical concentration detecting system according to claim 33, wherein said processing means uses said set of data to interpolate or extrapolate a relative concentration corresponding to the sensed electrical property value.

46. A chemical concentration detecting system according to claim 45, wherein said processing means normalizes said relative concentration to provide an absolute concentration of the antimicrobial chemical component of the decontamination solution.

47. A chemical concentration detecting system according to claim 33, wherein said system further comprises:

a bridge circuit, wherein said capacitor forms a part of said bridge circuit.

48. A chemical concentration detecting system according to claim 47, wherein said bridge circuit includes a potentiometer having first and second resistances associated therewith, said processing means determining values of said first and second resistances when the bridge circuit is in a null condition to determine said sensed electrical property value.

49. A method for determining whether rinse water used during a decontamination process is devoid of an antimicrobial chemical component, said method comprising:

exposing a capacitor, having first and second plates, to the rinse water, said rinse water comprising a dielectric therebetween;

sensing an electrical property of the capacitor to obtain a sensed electrical property value, said sensed electrical property value varying according to the concentration of the antimicrobial chemical component in the rinse water; and determining whether the sensed electrical property is indicative of the presence of an antimicrobial chemical component in the rinse water by accessing pre-stored data.

50. A chemical concentration detecting system according to claim 1, wherein said base fluid is selected from a group consisting of: water, an alcohol, a glycol containing chemical compound thereof.

51. A chemical concentration detecting system according to claim 50, wherein said glycol-containing chemical compound is selected from a group consisting of: polyethylene glycol, diethylene glycol triethylene glycol, tetraethylene glycol, glycol ethers, polypropylene glycol, propylene glycol, and combinations thereof.

52. A chemical concentration detecting system according to claim 50, wherein said alcohol is a tertiary alcohol.

* * * * *